United States Patent
Zacharie et al.

(10) Patent No.: US 8,637,574 B2
(45) Date of Patent: Jan. 28, 2014

(54) SALTS OF 3-PENTYLPHENYLACETIC ACID AND PHARMACEUTICAL USES THEREOF

(75) Inventors: Boulos Zacharie, Québec (CA); Christopher Penney, Québec (CA); Lyne Gagnon, Québec (CA); Jean-Francois Bienvenu, Québec (CA); Valérie Perron, Québec (CA); Brigitte Grouix, Québec (CA)

(73) Assignee: Prometic Biosciences, Inc., Mont-Royal, Quebec (CA)

( * ) Notice: Subject to any disclaimer, the term of this patent is extended or adjusted under 35 U.S.C. 154(b) by 0 days.

(21) Appl. No.: 13/318,252

(22) PCT Filed: May 3, 2010

(86) PCT No.: PCT/CA2010/000691
§ 371 (c)(1),
(2), (4) Date: Dec. 27, 2011

(87) PCT Pub. No.: WO2010/127448
PCT Pub. Date: Nov. 11, 2010

(65) Prior Publication Data
US 2012/0095102 A1    Apr. 19, 2012

Related U.S. Application Data

(60) Provisional application No. 61/175,215, filed on May 4, 2009.

(51) Int. Cl.
*A01N 37/10* (2006.01)
*A61K 31/19* (2006.01)

(52) U.S. Cl.
USPC .......................... 514/570; 514/557; 514/568

(58) Field of Classification Search
USPC .................. 514/553, 557, 568, 570
See application file for complete search history.

(56) References Cited

U.S. PATENT DOCUMENTS

| 3,228,831 | A | | 1/1966 | Nicholson et al. | |
| 3,385,886 | A | * | 5/1968 | Nicholson et al. | 562/492 |
| 3,385,887 | A | * | 5/1968 | Adams et al. | 562/496 |
| 3,894,080 | A | * | 7/1975 | Diamond et al. | 562/426 |
| 2012/0088784 | A1 | * | 4/2012 | Zacharie et al. | 514/277 |

OTHER PUBLICATIONS

Ortar et al., "New N-Arachidonoylserotonin Analogues with Potential "Dual" Mechanism of Action against Pain", *Journal of Medicinal Chemistry*, 2007, vol. 50, No. 26, pp. 6554-6569.

* cited by examiner

*Primary Examiner* — My-Chau T Tran
(74) *Attorney, Agent, or Firm* — Saliwanchik, Lloyd & Eisenschenk

(57) ABSTRACT

The present invention relates to salts of 3-pentylphenylacetic acid and their pharmaceutical uses. Particular aspects of the invention relate to the use of those salts in the prevention and/or treatment of various diseases and conditions in subjects, including the prevention and treatment of (i) blood disorders, (ii) renal disorders and renal disorder complications; (iii) inflammatory-related diseases; and/or (iv) oxidative stress related disorders.

25 Claims, 6 Drawing Sheets

SALTS OF 3-PENTYLPHENYLACETIC ACID AND PHARMACEUTICAL USES THEREOF

CROSS REFERENCE TO A RELATED APPLICATION

This application is a National Stage Application of International Application Number PCT/CA2010/000691, filed May 3, 2010; which claims priority to U.S. Provisional Application No. 61/175,215, filed May 4, 2009; which are incorporated herein by reference in their entirety.

FIELD OF INVENTION

The present invention concerns salts of 3-pentylphenylacetic acid and their pharmaceutical uses. More particularly, the invention relates to a sodium salt of 3-pentylphenylacetic acid, to a process for its preparation, to compositions comprising same and to its use for the prevention or treatment of various diseases and conditions in subjects.

BACKGROUND OF INVENTION

Blood disorders

Hematopoiesis (hema=blood) refers to the process of formation, development and differentiation of all types of blood cells. All cellular blood components are derived from haematopoietic stem cells, including leukocytes and erythrocytes. The leukocytes or white blood cells (WBCs) are the cells of the immune system defending the body against both infectious disease and foreign materials. The erythrocytes are the non-nucleated, biconcave, disk-like cells which contain hemoglobin and these cells are essential for the transport of oxygen. A reduction in the number of white blood cells is called leukopenia whereas anemia refers to that condition which exists when there is a reduction below normal in the number of erythrocytes, the quantity of hemoglobin, or the volume of packed red blood cells in the blood. Disorders of the blood and the several kinds of leukopenia and anemia may be produced by a variety of underlying causes, including chemotherapy (e.g. chemotherapy induced anemia) and cancers (e.g. cancer related anemia). Therefore, there is a need for novel compositions and methods to stimulate hematopoiesis and to address the undesirable side effects of myelosuppression induced by chemotherapy and radiation therapy.

Kidney diseases

The kidney is a structurally complex organ that has evolved to perform a number of important functions: excretion of the waste products of metabolism, regulation of body water and salt, maintenance of appropriate acid balance, and secretion of a variety of hormones and autocoids. Diseases of the kidney are as complex as its structure, but their study is facilitated by dividing them by their effects on four basic morphologic components: glomeruli, tubules, interstitium, and blood vessels. Unfortunately, some disorders affect more than one structure and the anatomic interdependence of structures in the kidney implies that damage to one almost always secondarily affects the others. Thus, whatever the origin, there is a tendency for all forms of renal disease ultimately to destroy all four components of the kidney, culminating in chronic renal failure. For instance, in autoimmune diseases such as diabetes mellitus, the kidneys are prime targets to suffer tissue damage or lesions. Nephrectomy, or kidney removal, a procedure which is sometimes performed on patients with kidney cancer (e.g. renal cell carcinoma), may negatively impact kidney function in the remaining kidney. Chemotherapy and immunosuppressive therapy are also a source of harmful effects to the kidneys. Therefore, there exists a need for drugs with a good safety profile which can be administered to patients with kidney disease. There is also a need for pharmaceutical compounds which can prolong kidney health or protect it from deterioration to the point at which the kidney can no longer function.

Inflammation

Immune Mediated inflammatory Disease (IMID) refers to any of a group of conditions or diseases that lack a definitive etiology but which are characterized by common inflammatory pathways leading to inflammation, and which may result from, or be triggered by, a dysregulation of the normal immune response. Autoimmune disease refers to any of a group of diseases or disorders in which tissue injury is associated with a humoral and/or cell-mediated immune response to body constituents or, in a broader sense, an immune response to self. Current treatments for autoimmune disease can be broadly classified into two groups: those drugs which dampen or suppress the immune response to self and those drugs which address the symptoms that arise from chronic inflammation. In greater detail, conventional treatments for autoimmune diseases (e.g., primarily arthritis) are (1) Non-steroidal Anti-Inflammatory Drugs (NSAIDs) such as aspirin, ibuprofen, naproxen, etodolac, and ketoprofen; (2) Corticosteroids such as prednisone and dexamethasone; (3) Disease-Modifying Anti-Rheumatic Drugs (DMARDs) such as methotrexate, azathioprine, cyclophosphamide, cyclosporin A, Sandimmune™, Neoral™, and FK506 (tacrolimus); (4) Biologicals such as the recombinant proteins Remicade™, Enbrel™ and Humira. While numerous therapies are available, conventional treatments are not routinely efficacious. More problematic is the accompanying toxicity which often prohibits the long-term use necessary with a chronic disease. Therefore, there is a need for compounds that are useful for the treatment of inflammatory-related diseases, including chronic and non-chronic autoimmune disease.

Oxidative Stress

Oxidative stress is caused by an imbalance between the production of reactive oxygen species and a biological system's ability to readily detoxify the reactive intermediates or easily repair the resulting damage. Although reactive oxygen species can be beneficial, as they are used in cell signaling and by the immune system they are also involved in many diseases. Therefore, a need still exists for compounds which can help maintain a proper balance in levels of reactive oxygen species in order to prevent damage to the cell or its components that may be caused by toxic effects of such reactive species.

The present invention addresses these needs for new treatment methods, compounds, and pharmaceutical compositions.

As part of their on-going investigation into new chemical entities for use in the treatment of the aforesaid diseases, the inventors have invented salts of 3-pentylphenylacetic acid. The invention is not concerned with non-salt versions of 3-pentylphenylacetic acid because this acid is extremely difficult to handle and is difficult to characterize owing to its hygroscopicity.

Prior to the present invention salts of 3-pentylphenylacetic acid as defined herein were unknown. It was also unknown to use salts of 3-pentylphenylacetic acid for the prevention and/or treatment of (i) blood disorders, (ii) renal disorder and or a renal disorder complication; (iii) an inflammatory-related disease; and/or (iv) oxidative stress related disorder.

Additional features of the invention will be apparent from review of the disclosure, figures and description of the invention below.

BRIEF SUMMARY OF THE INVENTION

The present invention relates to salts, compositions and treatment regimens for the prevention and/or treatment of various diseases and conditions in subjects.

One particular aspect of the invention concerns salts of 3-pentylphenylacetic acid and their use in preventing and/or treating (i) blood disorders (e.g. anemia, neutropenia) (ii) renal disorders and/or renal disorder complications; (iii) inflammatory-related diseases (e.g. autoimmune disease); and (iv) oxidative stress.

Another related aspect of the invention concerns the use of a salt represented by any of the formulas as defined herein for the manufacture of a medication and/or for the manufacture of medications and pharmaceutical compositions. One particular example is a nephroprotective composition comprising a salt of 3-pentylphenylacetic acid as defined herein, and a pharmaceutically acceptable carrier.

The invention further relates to methods of preventing and/or treating various diseases and conditions including, but not limited to: (i) blood disorders (e.g. anemia, neutropenia) (ii) renal disorders and/or renal disorder complications; (iii) inflammatory-related diseases (e.g. autoimmune disease); and/or (iv) oxidative stress. The method comprises administering to a human patient in need thereof a pharmacologically effective amount of a salt represented by any of the formulae as defined herein. The salt may be selected from the group consisting of lithium, sodium, and potassium. Preferably, the salt is a sodium salt.

The invention further relates to salts as defined herein as prophylactically effective and/or therapeutically effective agents against various diseases and conditions in subjects.

Further aspects of the invention will be apparent to a person skilled in the art from the following description, and claims and generalizations therein.

BRIEF DESCRIPTION OF THE FIGURES

In order that the invention may be readily understood, embodiments of the invention are illustrated by way of examples in the accompanying drawings.

DETAILED DESCRIPTION OF THE INVENTION

A) General Overview of the Invention

Figure 1:
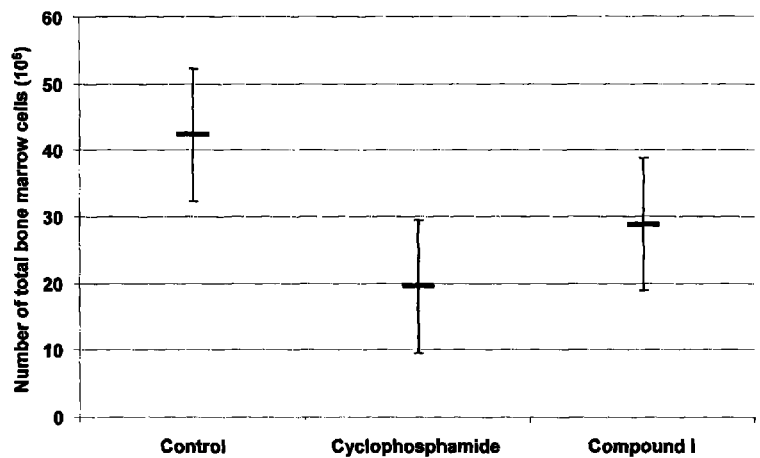
FIG. 1 is a dot graph showing effect of Compound I on total bone marrow cell counts in control and cyclophosphamide treated mice.

The present inventors have synthesized salts of 3-pentylphenylacetic acid. The present inventors have discovered that salts of 3-pentylphenylacetic acid have beneficial pharmaceutical properties and that these salts may be effective for use in the development of blood cells, in kidney protection, in inflammatory diseases and against oxidative stress-related disorders.

B) Salts of the Invention

A salt of the present invention is represented by the following formula:

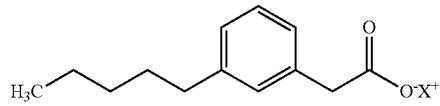

wherein $X^+$ is a base addition salt.

The base addition salt is a pharmaceutically acceptable base addition salt.

In all embodiments described herein, the free acid (i.e. non-salt form) 3-pentylphenylacetic acid is explicitly excluded from the scope of the invention.

As used herein, the term "pharmaceutically acceptable base addition salt" is intended to mean those salts which retain the biological effectiveness and properties of the free acid, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

One example of a salt of the present invention is a sodium salt and is represented by the formula:

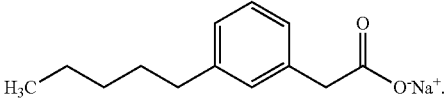

Advantageously, the sodium salt of 3-pentylphenylacetic acid (hereinafter "Compound I") is well characterized, as described hereinbelow. The salt is a white solid, which has a defined melting point, and is easy to handle. Furthermore, the sodium salt is not hygroscopic and is very water soluble.

Pharmaceutically acceptable base salts may be synthesized from the parent agent that contains an acidic moiety, by conventional chemical methods. Generally, such salts are prepared by reacting the free acid forms of these agents with a stoichiometric amount of the appropriate base in water or in an organic solvent, or in a mixture of the two. Salts may be prepared in situ, during the final isolation or purification of the agent or by separately reacting a purified synthetic intermediate compound in its free acid form with the desired corresponding base, and isolating the salt thus formed. Example of pharmaceutically acceptable salts are described, for example, in Berge et al., "Pharmaceutical Salts", *J. Pharm. Sci.* 66, 1-19 (1977).

If any substituents in an intermediate compound are used to synthesize the above described salts are incompatible with the synthetic methods of the present invention, the substituents may be protected with a suitable protecting group that is stable to the reaction conditions used in these methods. The protecting group may be removed at a suitable point in the reaction sequence of the method to provide a desired intermediate or target salt. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3.sup.rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a salt.

Hydrates

In addition, the salts of the invention also may exist in hydrated and anhydrous forms. Hydrates of any of the salts described herein are included as salts of the invention which may exist as a monohydrate or in the form of a polyhydrate.

C) Methods of Preparation

The present inventors have discovered that a modified Sonogashira coupling reaction can be used to synthesize intermediate compounds for use in synthesizing salts of the present invention. Generally speaking, Sonogashira coupling reactions may be represented as follows:

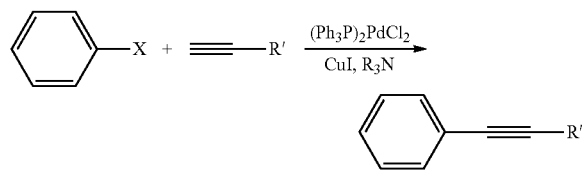

where X is a halogen, typically bromine, $R_3N$ is a base such as triethylamine and R' is a carbon chain.

Typically, two catalysts are needed for this reaction, namely a zerovalent palladium complex and a halide salt of copper(I). The palladium complex activates the organic halides and the copper(I) halides react with the terminal alkyne and produce copper(I) acetylide, which acts as an activated species for the coupling reactions. The reaction medium must be basic to neutralize the hydrogen halide produced as the byproduct of this coupling reaction, thus alkyl amine compounds such as triethylamine and diethylamine are typically used as solvents, although DMF or diethyl ether can also be used as solvent.

In this modified procedure, the inventors have used Pd(II) and eliminate the use of the second catalyst (copper(I) halides) and alkyl amine (triethylamine). The reaction is generally applied for all halo substituted phenyl alkyl carboxylic esters. Also this advantageously allows for a simpler workup. The inventors' discovery was thus applied to the synthesis of ethyl [3-[pentyne-1-yl]phenyl]acetate, an intermediate used to synthesize the sodium salt of 3-pentyl phenyl acetate. A reaction scheme is provided in the Exemplification section. Thus, accordingly there is provided a process for preparing the sodium salt of 3-pentylphenylacetic acid, the process comprising:

a) heating a mixture of ethyl [3-bromophenyl]acetate and 1-pentyne in the presence of tetrabutylammonium fluoride hydrate and $PdCl_2(PPh_3)_2$ to provide ethyl [3-[pentyne-1-yl]phenyl]acetate;

b) reducing the ethyl [3-[pentyne-1-yl]phenyl]acetate to provide ethyl [3-[pentyl-1-yl]phenyl]acetate; and c) hydrolyzing ethyl [3-[pentyl-1-yl]phenyl]acetate so to produce the sodium salt of 3-pentylphenylacetic acid.

In one example, the heating step is carried out in a sealed tube. In one embodiment, the tube is heated at 80° C. for 2 h.

In one example, the ethyl [3-[pentyne-1-yl]phenyl]acetate is reduced using hydrogenation in the presence of palladium on charcoal as a catalyst.

In one example, the ethyl ester is hydrolyzed using lithium hydroxide in a solvent mixture that includes tetrahydrofuran, methanol and water. One skilled in the art will readily recognize that the ethyl ester may be hydrolyzed using any number of hydrolysing techniques known in the art of organic chemistry.

In one example, the intermediate free acid, 3-pentylphenylacetic acid is hydrolyzed using sodium hydrogen carbonate in an ethanol/water solvent mixture.

D) Pharmaceutical Applications

As indicated herein before and exemplified hereinafter, the salts of the invention have beneficial pharmaceutical properties and these salts may have pharmaceutical applications in the prevention and/or treatment of various diseases and conditions in a subject. Medical and pharmaceutical applications contemplated by the inventors include, but are not limited to, those addressing blood disorders, renal failure, inflammatory-related diseases and disorders related to reactive oxygen species.

The term "subject" includes living organisms in which blood disorders, renal failure, inflammatory-related diseases and/or oxidative stress-related disorders, can occur, or which are susceptible to such conditions. The term "subject" includes animals such as mammals or birds. Preferably, the subject is a mammal. More preferably, the subject is a human. Even more preferably, the subject is a human patient in need of treatment.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms "treatment" or "treating" of a subject includes the application or administration of a salt of the invention to a subject (or application or administration of a salt of the invention to a cell or tissue from a subject) with the purpose of delaying, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being. In some embodiments, the term "treating" can include increasing a subject's life expectancy and/or delay before additional treatments are required (e.g. dialysis or kidney transplantation).

Blood Disorders and Hematopoiesis

Addressing blood disorders is among the medical and pharmaceutical applications contemplated by present invention. The term "blood disorder" refers to any alteration in normal physiology, formation, proliferation and/or function of erythrocytes, leukocytes and/or platelets. Therefore, in one of its aspects the present invention relates to methods, salts and compositions for stimulating hematopoiesis in a subject, preferably a human patient in need thereof.

Accordingly, one aspect of the invention relates to the use of the salts described herein for stimulating production of leukocytes in a subject and/or for inhibiting decrease of leukocytes (i.e. leukopenia or leukocytopenia) in a subject. Related aspects include using of these salts for stimulating a subject's immune system and reduce a subject's risk for infection. In some embodiment, the leukocytes are neutrophil granulocytes and the disorder is neutropenia. As is known, low white cell counts are often associated with chemotherapy, radiation therapy, leukemia, myelofibrosis and aplastic anemia. In addition, many common medications can cause leukopenia (e.g. minocyclen, a commonly prescribed antibiotic). Accordingly, the invention also relates to the use of the salts described herein for the prevention and/or treatment of those particular diseases and conditions.

In order to evaluate, assess, and/or confirm the efficacy of the method, salts and/or compositions of the invention, serial measurements can be determined. Quantitative assessment of blood cell count, hematopoiesis and erythropoiesis are well known in the art.

Typically a normal total white blood cell count in humans is within the range of 4 300 to 10 000 per $mm^3$ (or mL), with an average value taken as 7 000 per $mm^3$. A normal neutrophil count in human blood is within the range of 1 800 to 7 200 per $mm^3$. Therefore, leukopenia refers to the condition wherein the blood white cell or leukocyte count is reduced to 5 000 per $mm^3$ or less. In some embodiments, the subject is a human patient having a total white blood cells count under about 8 000 per $mm^3$, or under about 5 000 per $mm^3$ or under about 4 000 per $mm^3$, or under 3 000 per $mm^3$. In some embodiments, the subject is a human patient having a total neutrophil granulocytes count under about 5 000 per $mm^3$, or under about 4 000 per $mm^3$, or under about 3 000 per $mm^3$, or under about 2 000 per $mm^3$, or under about 1 000 per $mm^3$. In some embodiments, the methods, compounds or compositions of the invention are effective in increasing the patients' total white blood cells count (and/or neutrophil granulocytes count) by at least 500 per $mm^3$, by at least 1 000 per $mm^3$, or by at least 2 000 per $mm^3$ or more.

Another aspect of the invention relates to the use of the salts described herein for stimulating production of erythrocytes (i.e. erythropoiesis) in a subject and/or inhibiting decrease of erythrocytes (i.e. anemia) in a subject. Related aspects include using of these salts for compensating for excessive blood loss (e.g. a hemorrhage or chronically through low-volume loss), excessive blood cell destruction (e.g. hemolysis) or deficient red blood cell production (e.g. ineffective hematopoiesis). Related aspects include using of these salts for blood cell differentiation, including the stimulation of production of erythrocytes from erythroid progenitor cells.

Of particular interest to the inventors is addressing anemia associated with the use of chemotherapy or radiotherapy in the treatment of cancer. Also of particular interest is anemia associated with end-stage renal disease as is the case for patients who require regular dialysis or kidney transplantation for survival. Therefore, some aspects of the invention relates to methods, compounds and compositions for the stimulation of the hematopoietic system in humans, for instance for treating the myelosuppressive effects of chemotherapy and/or radiotherapy and any other situation in which the stimulation of the hematopoietic system can be of therapeutic value such as, but not limited to, anemia. Additional aspects of the invention relates to a method effective for increasing the efficacy of chemotherapy and/or radiation therapy in human patients. The methods, compounds and compositions according to the invention may also be useful for using increasing the dose of chemotherapeutic compositions necessary to achieve a better therapeutic benefit, while avoiding increased side effects. Additional aspects relates to the methods, compounds and compositions according to the invention for reducing or eliminating chemotherapy-induced anemia in humans.

Typically, in normal adults, average values for red blood cell count (millions/$mm^3$), hemoglobin (g/100 mL) and hematocrit or volume packed red blood cells (mL/100 mL) for females and males (at sea level) are 4.8+/−0.6 and 5.4+/−0.9, 14.0+/−2.0 and 16.0+/−2.0 and 52.0+/−5.0 and 47.0+/−5.0 respectively. Anemia refers to the condition which exists when there is a reduction below normal in the number of erythrocytes, the quantity of hemoglobin or the volume of packed red blood cells in the blood as characterized by a determination of the hematocrit. In some embodiments, the subject is a human patient having an hematocrit between 40 and 30, or under about 40. In some embodiments, the methods, compounds or compositions of the invention are effective in slowing a decrease or maintaining the patients' total red blood cells count and/or hematocrit. In some embodiments, the methods, compounds or compositions of the invention are effective stabilizing the patients' hematocrit and/or in increasing the hematocrit by up about 5, or about 10, or whatever is necessary to achieve a normal value. In some embodiments, the methods, compounds or compositions of the invention are effective in reducing the need for blood transfusion(s).

Kidney Protection

In some aspects, the present invention relates to methods, salts and compositions for preventing and/or treating a renal disorder in a subject in need thereof. The term "renal disorder", "renal disease" or "kidney disease" means any alteration in normal physiology and function of the kidney. This can result from a wide range of acute and chronic conditions and events, including physical, chemical or biological injury, insult, trauma or disease, such as for example nephrectomy, chemotherapy, hypertension, diabetes, congestive heart failure, lupus, sickle cell anemia and various inflammatory, infectious and autoimmune diseases, HIV-associated nephropathies etc. This term includes but is not limited to diseases and conditions such as kidney transplant, nephropathy; chronic kidney disease (CKD); glomerulonephritis; inherited diseases such as polycystic kidney disease; nephromegaly (extreme hypertrophy of one or both kidneys); nephrotic syndrome; end stage renal disease (ESRD); acute and chronic renal failure; interstitial disease; nephritis; sclerosis, an induration or hardening of tissues and/or vessels resulting from causes that include, for example, inflammation due to disease or injury; renal fibrosis and scarring; renal-associated proliferative disorders; and other primary or secondary nephrogenic conditions. Fibrosis associated with dialysis following kidney failure and catheter placement, e.g., peritoneal and vascular access fibrosis, is also included.

In some embodiments the present invention more particularly relates to methods, compounds and compositions for nephroprotection. As used herein, "nephroprotection" refers to a process by which the rate of disease progression in the kidney is delayed or stopped and so the kidney is subsequently protected. In preferred embodiments (e.g. drug-induced nephrotoxicity), the compounds of Formula I are be administered prior to, during, or subsequent to the administration of a cytotoxic agent or anti-inflammatory or immunosuppressive drug. "Cytotoxic agent" refers to an agent which kills highly proliferating cells: e.g., tumors cells, virally infected cells, or hematopoietic cells. Examples of a cytotoxic agent include, but are not limited to, cyclophosphamide, doxorubicin, daunorubicin, vinblastine, vincristine, bleomycin, etoposide, topotecan, irinotecan, taxotere, taxol, 5-fluorouracil, methotrexate, gemcitabine, cisplatin, carboplatin, or chlorambucil, and an agonist of any of the above compounds. A cytotoxic agent can also be an antiviral agent: e.g., AZT (i.e., 3'-azido-3'-deoxythymidine) or 3TC/lamivudine (i.e., 3-thiacytidine). Such drugs can induce anemia in a mammal, including a human patient. In some embodiments, nephroprotection refers to the protection provided to a mammal from the toxic effects arising from treatment of the mammal with a chemotherapeutic agent. For instance, the compounds of Formula I may be used to protect the mammal, or facilitate its recovery of the animal, from the toxic effects resulting from treatment of the mammal with a chemotherapeutic agent.

In some embodiments, the renal disorder or kidney disease may be generally defined as a "nephropathy" or "nephropathies". The terms "nephropathy" or "nephropathies" encompass all clinical-pathological changes in the kidney which may result in kidney fibrosis and/or glomerular diseases (e.g. glomerulosclerosis, glomerulonephritis) and/or chronic renal insufficiency, and can cause end stage renal disease and/or renal failure. Some aspects of the present invention relate to compositions and their uses for the prevention and/or treatment of hypertensive nephropathy, diabetic nephropathy, and other types of nephropathy such as analgesic nephropathy, immune-mediated glomerulopathies (e.g. IgA nephropathy or Berger's disease, lupus nephritis), ischemic nephropathy, HIV-associated nephropathy, membranous nephropathy, glomerulonephritis, glomerulosclerosis, radiocontrast media-induced nephropathy, toxic nephropathy, analgesic-induced nephrotoxicity, cisplatin nephropathy, transplant nephropathy, and other forms of glomerular abnormality or injury; glomerular capillary injury (tubular fibrosis). In some embodiments, the terms "nephropathy" or "nephropathies" refers specifically to a disorder or disease where there is either the presence of proteins (i.e. proteinuria) in the urine of a subject and/or the presence of renal insufficiency.

The present invention further relates to methods, salts and compositions for preventing and/or treating a renal disorder complication. The term "renal disorder complication" refers to a secondary condition correlated with a renal disorder, a health condition, an accident, or a negative reaction occurring during the course of a renal disorder that can become worse in its severity. A "renal disorder complication" is usually associated with increasing severity of the renal disease in the subjects suffering from symptoms or pathological changes, which can become widespread throughout the body or affecting other organ systems. As used herein, the term "renal disorder complication" encompasses, but is not limited to vascular diseases (e.g., macrovascular complications, microvascular complications, etc.), cardiovascular diseases (e.g. arteriosclerosis, atherosclerosis, coronary artery disease, congestive heart failure, stroke, angina, ischemic heat disease, myocardial infarction, etc), diabetic dyslipidemia, hyperlipidemia (e.g. hypercholesterolemia, hypertriglyceridemia, hyperlipoproteinemia), metabolic syndrome, obesity, anemia, edema, pancreatitis, weak bones, poor nutritional health and nerve damage.

According to some embodiments, the present invention concerns methods, salts and compositions for preventing or treating characteristic aspects or evidence nephropathy including glomerulosclerosis, modification of the kidney vascular structure, and tubulointerstitial disease. Among characteristic aspects of nephropathy contemplated by the invention is the prevention of kidney cell apoptosis, fibrosis, sclerosis, and/or accumulation of proteins in tubular regions. Related aspects concerns the use of the salts and pharmaceutical compositions as defined herein for reducing CTGF mRNA expression and/or TGF-β mRNA expression in kidney cells.

In some embodiments, the subject may be suffering from a disorder such as, for example, diabetes, advanced progressive renal disease, and fibrotic renal disease and/or any of the renal diseases, renal disorders or renal disorder complications described herein. In some embodiments, the subject is a human patient having or susceptible of having glomerular filtration problems and/or a renal failure. In some embodiments, the subject is a human patient who is following, or who has received, treatments of chemotherapy or radiotherapy. Accordingly, related aspect concerns using the salts or pharmaceutical compositions as defined herein for protecting kidneys against chemotherapeutic agents, including, but not limited to, doxorubicin, daunorubicin, vinblastine, vincristine, bleomycin, taxol, 5-fluorouracil, methotrexate, gemcitabine, cisplastin, carboplatin and chlorambucil. The methods of the present invention may comprise administering to a subject, e.g., a human patient in need thereof, a preventative- or therapeutically-effective amount of a salt or pharmaceutical composition as defined herein.

In order to evaluate, assess, and/or confirm the efficacy of the method, salts and/or compositions of the invention, serial measurements can be determined. Quantitative assessment of renal function and parameters of renal dysfunction are well known in the art and can be found, for example, in Levey (Am J Kidney Dis. 1993, 22(I):207-214). Examples of assays for the determination of renal function/dysfunction are: serum creatinine level; creatinine clearance rate; cystatin C clearance rate, 24-hour urinary creatinine clearance, 24-hour urinary protein secretion; glomerular filtration rate (GFR); urinary albumin creatinine ratio (ACR); albumin excretion rate (AER); and renal biopsy.

In some embodiments, the subject is at risk of, or has been diagnosed with, nephropathy. Typically a normal glomerular filtration rate (GFR) in humans is from about 100 to about 140 ml/min. In some embodiments, the subject is a human patient having advanced nephropathy (i.e. a GFR of under 75 ml/min). In some embodiments, the subject is a human patient having ESRD (i.e. GFR of less than 10 ml/min). In some embodiments, the methods, salts or compositions of the invention are effective in increasing the patients' GFR value by at least 1, 5, 10, 15, 20 or 25 ml/min or more.

In some embodiments, the subject is at risk of, or has been diagnosed with, a kidney disease. In various embodiments, the subject is a human patient having or progressing towards stage I kidney disease, stage II kidney disease, stage III kidney disease, stage IV kidney disease or stage V kidney disease. In some embodiments, the methods, salts or compositions of the invention are effective in stabilizing or in improving the patient's kidney disease ((e.g. from stage V to stage IV, or from stage IV to stage III, or from stage III to stage II, or from stage II to stage I).

One of the first clinical indications of nephropathy is the presence of albuminuria or proteinuria. One refers to microalbuminuria when the amount of albumin in the urine is less than or equal to <300 mg/day and proteinuria when the total amount of protein in the urine is greater than 1 g/day. In some embodiments, the subject is at risk of, or has been diagnosed with, proteinuria. In some embodiments, the subject is a human patient producing less than about 300 mg/day of protein in its urine. In some embodiments, the subject is a human patient producing more than about 1 g/day of protein in its urine. In some embodiments, the subject is a human patient having microalbuminuria. In some embodiments, the subject is a human patient with an albumin amount in the urine that exceeds 200 µg/min. In some embodiments, the methods, salts or compositions of the invention are effective in lowering the patient's albuminuria by at least 10, 25, 50, 75, 100, 150, 200 µg/min or more.

Effectiveness of the methods, salts and compositions of the invention may be assessed by the reduction in the undesired symptoms. Such reduction may be determined for example by the improvement in renal function as compared to the function prior to treatment. Such remediation may be evident in a delay in the onset of renal failure (including dialysis or transplant) or in a decrease in the rate of the deterioration of renal function as determined for example by the slowing of the rate of the increase of proteinuria or slowing the rate of the rise in serum creatinine or by the fall in the parameter of creatinine clearance or GFR, or decrease in hospitalization rate or mortality. In some embodiments, the salt is the sodium salt of 3-pentylphenylacetic acid.

In one embodiment, a salt of the invention is used in combination with at least one additional known compound which is currently being used or in development for preventing or treating renal disorder such as nephropathy, or an associated disorder or complication. Examples of such known compounds include but are not limited to: ACE inhibitor drugs (e.g. captopril (Capoten®), enalapril (Innovace®), fosinopril (Staril®), lisinopril (Zestril®), perindopril (Coversyl®), quinapril (Accupro®), trandanalopril (Gopten®), lotensin, moexipril, ramipril); RAS blockers; angiotensin receptor blockers (ARBs) (e.g. Olmesartan, Irbesartan, Losartan, Valsartan, candesartan, eprosartan, telmisartan, etc); protein kinase C (PKC) inhibitors (e.g. ruboxistaurin); inhibitors of AGE-dependent pathways (e.g. aminoguanidine, ALT-946, pyrodoxamine (pyrododorin), OPB-9295, alagebrium); anti-inflammatory agents (e.g. cyclooxigenase-2 inhibitors, mycophenolate mophetil, mizoribine, pentoxifylline), GAGs (e.g. sulodexide (U.S. Pat. No. 5,496,807)); pyridoxamine (U.S. Pat. No. 7,030,146); endothelin antagonists (e.g. SPP 301), COX-2 inhibitors, PPAR-γ antagonists and other compounds like amifostine (used for cisplatin nephropathy), captopril (used for diabetic nephropathy), cyclophosphamide (used for idiopathic membranous nephropathy), sodium thiosulfate (used for cisplatin nephropathy), tranilast, and the like.

Inflammation

Another aspect of the invention relates to the use of the salts of the invention for the prevention and/or treatment of inflammatory-related diseases. The term "inflammatory-related disease" refers to any and all abnormalities associated with inflammation, including chronic and acute inflammatory diseases, including but not limited to immune mediated inflammatory diseases (IMID) and autoimmune diseases; arthritis, ITP, glomerulonephritis, vasculitis, psoriatic arthritis, systemic lupus erythematoses (SLE), idiopathic thrombocytopenic purpura (ITP), psoriasis, Crohn's disease, inflammatory bowel disease, ankylosing spondylitis, Sjögren's syndrome, Still's disease (macrophage activation syndrome), uveitis, scleroderma, myositis, Reiter's syndrome, and Wegener's syndrome. In general, prophylactic and therapeutic uses comprise the administration of a compound as described herein to a subject, preferably a human patient in need thereof. The salts of the invention may be administered with any conventional treatments, including more particularly the current treatments defined hereinbefore in the Background section. In order to evaluate, assess, and/or confirm the efficacy of the method, salts and/or compositions of the invention, serial measurements can be determined. Quantitative methods and techniques for the assessment of inflammation are well known in the art and include for instance methods similar to those provided in the exemplification section.

Additionally, or alternatively, salts of the present invention may inhibit the production of prostaglandins, including but not limited to PGE2, and thus be useful to reduce fever, pain, stiffness, and swelling.

Oxidative Stress

Another aspect of the invention relates to methods, salts and compositions of the invention for the prevention and/or treatment of an oxidative stress related disorder. The term "oxidative stress related disorder" refers to any disease in which there is an imbalance between the production of reactive oxygen species and a biological system's ability to readily detoxify the reactive intermediates or easily repair the resulting damage. Examples of such diseases include, but are not limited to, cardiovascular diseases, cancer, diabetes, arthritis, atherosclerosis, Parkinson's disease, heart failure, myocardial infarction, Alzheimer's disease, chronic fatigue syndrome and autoimmune diseases.

In general, prophylactic and therapeutic uses comprise the administration of a salt as described herein to a subject, preferably a human patient in need thereof. In some embodiments, the subject is at risk of, or has been diagnosed with an oxidative stress related disorder as defined hereinabove.

A related aspect of the invention relates to methods, salts and compositions for maintaining a proper balance in levels of reactive oxygen species, and more particularly nitric oxide (NO), in order to prevent damage to the cell or its components. An additional related aspect relates to methods, salts and compositions for preventing damage to a cell or its components (including but not limited to proteins, lipids and DNA) that may be caused by reactive species, and more particularly NO. Yet, a further aspect of the invention relates to the use of methods, salts and compositions according to the invention for inhibiting NO production and/or for inhibiting the enzyme nitric oxide synthase. These methods comprise contacting the cell, component or enzyme with a salt and/or a composition as defined herein. Quantitative methods and techniques for the assessment of reactive oxygen species levels in vitro and in vivo are well known in the art.

In general, prophylactic and therapeutic uses comprise the administration of a salt as described herein to a subject, preferably a human patient in need thereof. The salts of the invention may be administered with various antioxidants including, but not limited to, metal chelators/scavengers (e.g. desferrioxamine [Desferal®], a low molecular weight compound capable to scavenge $Fe^{3+}$ and other metal ions); low molecular weight scavengers of $\cdot O_2^-$ (superoxide), $\cdot OH$ (hydroxyl) or NO (nitric oxide) radicals (e.g. acetyl salicylic acid, scavenger of $\cdot O_2^-$; mannitol or captopril, scavengers of .OH; arginine derivatives, inhibitors of nitric oxide synthase which produce NO); and proteins or their fragments that can assist the protective action against reactive oxygen species (e.g. superoxide dismutase which breaks down $\cdot O_2^-$; hemoglobin which traps NO, catalase, or glutathione peroxidase which can eliminate hydrogen peroxide).

E) Pharmaceutical Compositions and Formulations

A related aspect of the invention concerns pharmaceutical compositions comprising the salts of the invention described herein. As indicated hereinbefore, the salts of the invention may be useful in: (i) in preventing and/or treating blood disorders (e.g. by stimulating hematopoiesis); (ii) in preventing and/or treating a renal disorder, a nephropathy, and/or a renal disorder complication; (iii) in preventing and/or treating a inflammatory-related disease (e.g. an autoimmune disease); and/or (iv) in the prevention and/or treatment of an oxidative stress related disorder.

As used herein, the term "therapeutically effective amount" means the amount of a salt that, when administered to a subject for treating or preventing a particular disorder, disease or condition, is sufficient to effect such treatment or prevention of that disorder, disease or condition. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the salt to have upon the subject and the properties of the salts (e.g. bioavailability, stability, potency, toxicity, etc), and the particular disorder(s) the subject is suffering from. In addition, the therapeutically effective amount may depend on the subject's blood parameters (e.g. lipid profile, insulin levels, glycemia), the severity of the disease state, organ function, or underlying disease or complications. Such appropriate doses may be determined using any available assays including the assays described herein. When one or more of the salts of the invention is to be administered to humans, a physician may for example, prescribe a relatively low dose at first, subsequently increasing the dose until an appropriate response is obtained.

As used herein, the term "pharmaceutical composition" refers to the presence of a salt of the present invention as defined herein and at least one pharmaceutically acceptable vehicle. An example of a salt of the present invention is the sodium salt of 3-pentylphenylacetic acid.

"Pharmaceutically acceptable vehicle" refers to a diluent, adjuvant, excipient, or carrier with which a salt is administered. The term "pharmaceutically acceptable" refers to drugs, medicaments, inert ingredients etc., which are suitable for use in contact with the tissues of humans and lower animals without undue toxicity, incompatibility, instability, irritation, allergic response, and the like, commensurate with a reasonable benefit/risk ratio. It preferably refers to a salt or composition that is approved or approvable by a regulatory agency of the Federal or State government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin.

In one embodiment, the compositions of the present invention may be manufactured by mixing the sodium salt of 3-pentylphenylacetic acid with a pharmaceutically acceptable vehicle.

In some embodiments, the compositions of the invention comprise an effective amount of the sodium salt of 3-pentylphenylacetic acid.

In some embodiments the invention pertains to pharmaceutical compositions for preventing and/or treating blood disorders that includes the sodium salt of 3-pentylphenylacetic acid as defined herein.

In some embodiments the invention pertains to pharmaceutical compositions for preventing and/or treating a renal disorder, a nephropathy, and or a renal disorder complication, the composition comprising the sodium salt of 3-pentylphenylacetic acid as defined herein.

In some embodiments the invention pertains to pharmaceutical compositions for preventing and/or treating a inflammatory-related disease, the composition comprising the sodium salt of 3-pentylphenylacetic acid as defined herein.

In some embodiments the invention pertains to pharmaceutical compositions for preventing and/or treating an oxidative stress related disorder, the composition comprising the sodium salt of 3-pentylphenylacetic acid as defined herein.

The salts of the invention may be formulated prior to administration into pharmaceutical compositions using available techniques and procedures. For instance, the pharmaceutical compositions may be formulated into suitable administration (orally, parenterally, (intravascular (IV), intraarterial (IA), intramuscular (IM), depo-IM, subcutaneous (SC), and depo SC), sublingually, intranasally (inhalation), intrathecally, topically, or rectally.

Preferably, the salts of the invention can be orally administered. The formulations may conveniently be presented in unit dosage form and may be prepared by any methods well known in the art of pharmacy. Methods of preparing these formulations or compositions include the step of bringing into association a salt of the present invention with a pharmaceutically acceptable vehicle (e.g. an inert diluent or an assimilable edible carrier) and, optionally, one or more accessory ingredients. In general, the formulations are prepared by uniformly and intimately bringing into association a salt of the present invention with liquid carriers, or finely divided solid carriers, or both, and then, if necessary, shaping the product. The amount of the therapeutic agent in such therapeutically useful compositions is such that a suitable dosage will be obtained.

Formulations of the invention suitable for oral administration may be in the form of capsules (e.g. hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles or as mouth washes and the like, each containing a predetermined amount of a salt of the present invention as an active ingredient. A salt of the present invention may also be administered as a bolus, electuary or paste, or incorporated directly into the subject's diet. Moreover, in certain embodiments these pellets can be formulated to (a) provide for instant or rapid drug release (i.e., have no coating on them); (b) be coated, e.g., to provide for sustained drug release over time; or (c) be coated with an enteric coating for better gastrointestinal tolerability. Coating may be achieved by conventional methods, typically with pH or time-dependent coatings, such that the salt(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

In solid dosage forms for oral administration a salt of the present invention may be mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Peroral compositions typically include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions suitable for injectable use may include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

Pharmaceutical formulations are also provided which are suitable for administration as an aerosol, by inhalation. These formulations comprise a solution or suspension of the salts described herein or a plurality of solid particles of such salt(s). The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any Formula described herein, or a salt thereof, in any appropriate manner known in the art, such as by micronization. The size of the solid particles or droplets will be, for example, from about 1 to about 2 microns. In this respect, commercial nebulizers are available to achieve this purpose. A pharmaceutical formulation suitable for administration as an aerosol may be in the form of a liquid, the formulation will comprise a salt as described herein, in a carrier which comprises water. A surfactant may be present which lowers the surface tension of the formulation sufficiently to result in the formation of droplets within the desired size range when subjected to nebulization.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of a salt of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The salt(s) of the invention may also be administered parenterally, intraperitoneally, intraspinally, or intracerebrally. For such compositions, the salt(s) of the invention can be prepared in glycerol, liquid polyethylene glycols, and mixtures thereof and in oils. Under ordinary conditions of storage and use, these preparations may contain a preservative to prevent the growth of microorganisms.

The method of treatment of the present invention may also include co-administration of the salt of the present invention together with the administration of another therapeutically effective agent for the prevention and/or treatment of (i) blood disorders, (ii) renal disorder and/or a renal disorder complication; (iii) an inflammatory-related disease; and/or (iv) oxidative stress related disorder. Therefore, an additional aspect of the invention relates to methods of concomitant therapeutic treatment of a subject, comprising administering to a subject in need thereof an effective amount of a first agent and a second agent, wherein the first agent is as a salt of the present invention, and the second agent is for the prevention or treatment of any one of disorder or disease of (i) to (v) hereinbefore. As used herein, the term "concomitant" or "concomitantly" as in the phrases "concomitant therapeutic treatment" or "concomitantly with" includes administering a fist agent in the present of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g. a human).

Accordingly, the invention also relates to a method for preventing, reducing or eliminating a symptom or complication of any one of the above mentioned disease or condition. The method comprises administering, to a subject in need thereof, a first pharmaceutical composition comprising a salt of the invention and a second pharmaceutical composition comprising one or more additional active ingredients, wherein all active ingredients are administered in an amount sufficient to inhibit, reduce, or eliminate one or more symptoms or complications of the disease or condition to be treated. In one aspect, the administration of the first and second pharmaceutical composition is temporally spaced apart by at least about two minutes. Preferably the salt is the sodium salt of 3-pentylphenylacetic acid as defined herein. The second agent may be selected from the list of compounds given hereinbefore.

F) Kits

The salt(s) of the invention may be packaged as part of a kit, optionally including a container (e.g. packaging, a box, a vial, etc). The kit may be commercially used according to the methods described herein and may include instructions for use in a method of the invention. Any or all of the kit components optionally further comprise buffers.

The salt(s) of the invention may or may not be administered to a patient at the same time or by the same route of administration. Therefore, the methods of the invention encompass kits which, when used by the medical practitioner, can simplify the administration of appropriate amounts of two or more active ingredients to a patient.

A typical kit of the invention comprises a unit dosage form of a salt as defined herein, and a unit dosage form of at least one additional active ingredient. Examples of additional active ingredients that may be used in conjunction with the salts according to the invention, include, but are not limited to any of the compounds that could be used in combination with the salt(s) of the invention as indicated herein before.

Kits of the invention can further comprise devices that are used to administer the active ingredients. Examples of such devices include, but are not limited to, syringes, drip bags, patches, inhalers, enemas, and dispensers for the administration of suppository formulations.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles are provided hereinbefore.

Headings are included herein for reference and to aid in locating certain sections These headings are not intended to limit the scope of the concepts described therein under, and these concepts may have applicability in other sections throughout the entire specification Thus, the present invention is not intended to be limited to the embodiments shown herein but is to be accorded the widest scope consistent with the principles and novel features disclosed herein.

The singular forms "a", "an" and "the" include corresponding plural references unless the context clearly dictates otherwise.

Unless otherwise indicated, all numbers expressing quantities of ingredients, reaction conditions, concentrations, properties, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The invention is further illustrated by the following examples, which should not be construed as further limiting.

EXAMPLES

The Examples set forth hereinbelow provide exemplary methods for the preparation of the sodium salt of 3-pentylphenylacetic acid. Also provided are exemplary methods for assaying the sodium salt of 3-pentylphenylacetic acid of the invention for in vitro and in vivo efficacy.

Example 1

Detailed Experimental Procedures for the Preparation of the Sodium Salt of 3-pentylphenylacetic Acid (Hereinafter Compound I)

Instrumentation

All HPLC chromatograms and mass spectra were recorded on an HP 1100 LC-MS Agilent instrument using an analytical C18 column (250×4.6 mm, 5 microns) with a gradient over 5 min of 15-99% $CH_3CN$—$H_2O$ with 0.01% TFA as the eluant and a flow of 2 mL/min.

Compound I: Synthesis Using Modified Procedure of Sonogashira:

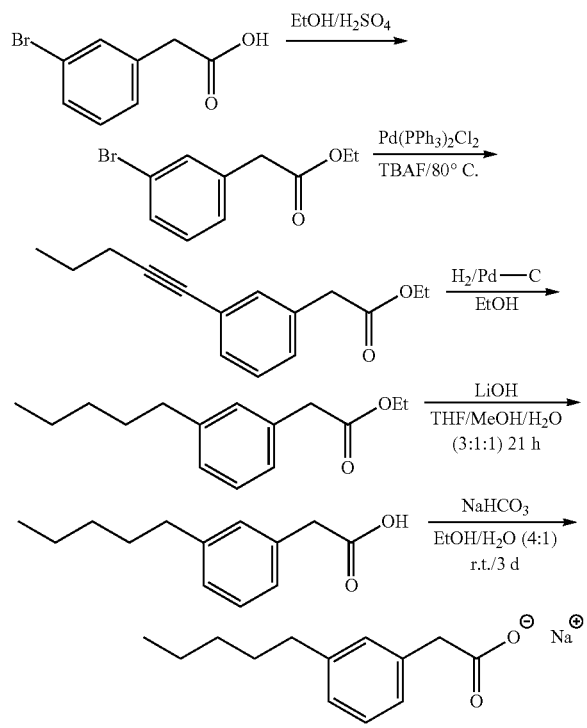

Step 1:

To a solution/suspension of 3-bromophenylacetic acid (5.02g, 23.33 mmol) in ethanol (100 mL) at room temperature was added concentrated sulfuric acid (1mL). The colorless solid was then stirred overnight at 80° C. The solution was concentrated under reduced pressure. The residue was diluted with ethyl acetate (25 mL), water (25 mL) and the two layers were separated. The aqueous layer was extracted with 2× ethyl acetate (25 mL) and brine (20 mL). The combined organic layers were washed with 2× saturated solution of $NaHCO_3$ (25 mL), brine (25 mL) and dried over sodium sulfate. After filtration the solution it was evaporated to dryness. This gave a light yellow oil (5.4 g, 95%). $^1H$—NMR (400 MHz, $CDCl_3$): δ 1.26 (t, J=4.7 Hz, 3H), 3.57 (s, 2H), 4.15 (Q, J=7.0 and 14.3 Hz, 2H), 7.17-7.26 (m, 2H), 7.38-7.44 (m, 1H), 7.44 (d, J=1.56 Hz, 1H).

Step 2:

A mixture of ethyl (3-bromophenyl)acetate (0.3 g, 1.24 mmol) and tetrabutylammonium fluoride hydrate (0.97 g, 3.72 mmol), was treated with $PdCl_2(PPh_3)_2$ (26 mg, 0.037 mmol; 3 mole %) and 1-pentyne (367 μl, 3.72 mmol) in a sealed tube. The tube was heated at 80° C. for 2 h. The mixture was treated with water, and was extracted with diethyl ether. The organic extract was dried over sodium sulfate, filtered and evaporated in vacuo to give the crude product. Purification on a Biotage™ 25M column (silica), eluting with ethyl acetate/hexane 0:1 to 2:98, gave ethyl (3-(pentyne-1-yl)phenyl)acetate as a pale yellow oil (0.23 g, 79%).

Step 3:

To ethyl[3-[pentyne-1-yl]phenyl]-acetate (0.23 g, 0.98 mmol) in ethanol (5 mL) under nitrogen atmosphere was added Pd on carbon (10%, 25 mg, 10% w/w). The mixture was vigorously stirred under hydrogen atmosphere at room temperature overnight. The solution was filtered and the palladium/carbon was washed with ethanol (20 mL). The filtrate was concentrated with silica gel. The crude product was purified by flash chromatography using a mixture of 10% hexanes/ethyl acetate. A clear oil was obtained (0.21 g, 90%).

Step 4:

To a solution of the ester (0.2 g, 0.9 mmol) in tetrahydrofuran (5 mL), methanol (1.5 mL) and water (1.5 mL) was added lithium hydroxide (0.09 g, 3.6 mmol) at 0° C. The reaction mixture was stirred overnight at room temperature. Insolubles were filtered and the filtrate was concentrated under reduced pressure. The residue was then treated with 2M HCl and extracted with ethyl acetate. The organic phase was dried over sodium sulfate and evaporated under reduced pressure. The crude material was purified on a 40 L Biotage column (silica) using ethyl acetate/hexanes (0:10 to 4:6) as eluant. This gave pure (3-pentylphenyl)acetic acid (0.19 g, 99%) as a white gummy solid. $^1H$ NMR (400 MHz, $CD_3OD$): δ 0.90 (t, J=7.0 Hz, 3H), 1.28-1.38 (m, 4 H), 1.61 (qt, J=7.6 Hz, 15.0 Hz, 2H), 2.58 (t, J=7.6 Hz, 2H), 3.56 (s, 2H), 7.07 (m, 3H), 7.20 (m, 1H); LRMS (ESI): m/z 207 ($MH^+$); HPLC: 4.3 min.

Step 5:

To a stirred solution of the acid (0.19 g, 0.82 mmol) in ethanol (4 mL) and water (1 mL) was added sodium bicarbonate (0.07 g, 0.82 mmol). The reaction mixture was stirred at room temperature overnight. The solvent was evaporated and the white gummy solid was dissolved in water and the solution was lyophilized. This gave pure sodium salt of (3-pentylphenyl)acetic acid (0.17 g, 92%) as a white solid. mp 110-112° C.; $^1H$ NMR (400 MHz, $CD_3OD$): δ 0.89 (t, J=6.8 Hz, 3H), 1.28-1.37 (m, 4 H), 1.60 (qt, J=7.4 Hz, 15.0 Hz, 2H), 2.56 (t, J=7.6 Hz, 2H), 3.43 (s, 2H), 6.96 (m, 1H), 7.12 (m, 3H); LRMS (ESI): m/z 207 (($MH^+$); HPLC: 4.3 min.

Example 2

Chemoprotection Studies

Female C57BU6 mice, 6 to 8 week old, were immunosuppressed by treatment with 200 mg/kg of cyclophosphamide administered intravenously at day 0. To examine the immunoprotective effect of Compound I, mice were pre-treated orally at day −3, −2 and −1 with the compound. Mice were sacrificed at day +5 by cardiac puncture and cervical dislocation. Then, a gross pathological observation of the femurs (as a source of bone marrow cells) was recorded. After the sacrifice, tissues were crushed in PBS buffer and cells were counted on a hemacytometer.

Figure 2:
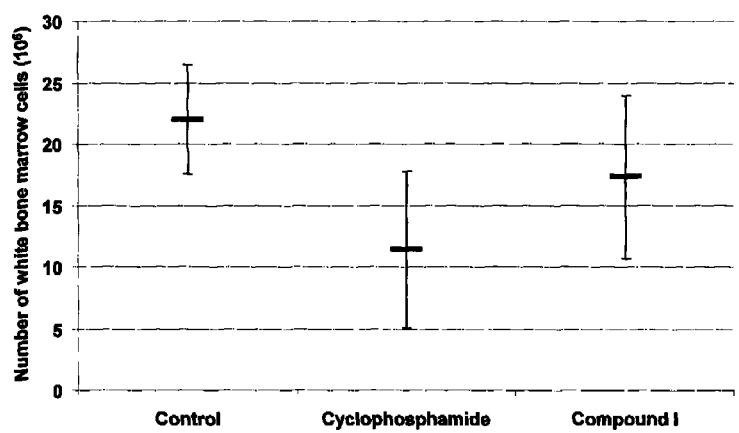
FIG. 2 is a dot graph showing effect of Compound I on total bone marrow cell counts of control and immunosuppressed mice.

A significant increase in total bone marrow cell count was observed with oral pre-treatment with Compound I in cyclophosphamide treated mice (FIG. 1). Furthermore, an increase in white bone marrow cell count was observed with oral pre-treatment with Compound I in cyclophosphamide immunosuppressed mice (FIG. 2).

Also, an increase in red bone marrow cell count was observed with oral pre-treatment with Compound I in cyclophosphamide immunosuppressed mice (Table 1). Furthermore, Compound I increases circulating red blood cells.

TABLE 1

Effect of Compound I on red bone marrow cell count and red blood cells

|  | Red Bone Marrow Cells ($10^6$) | Red Blood Cells ($10^9$) |
| --- | --- | --- |
| Control | 20.3 | 7.1 |
| Cyclophosphamide | 8.1 | 5.7 |
| Compound I | 11.5 | 7.0 |

Example 3

Effect of Compound I on Air-Pouch Model of Inflammation

LPS-induced inflammation in the rat air-pouch model is believed to mimic the pathological process occurring in joint diseases such as arthritis. This is because the connective tissues formed along the air pouch are similar to those found in chronic joint diseases. LPS-induced inflammation and chronic joint diseases share other features, including markedly elevated $PGE_2$, neutrophil infiltration, cytokine formation, and tissue damage.

An air cavity was produced at day −6 by subcutaneous injection of 20 ml of sterile air into the intrascapular area of the back of male Lewis rats (175-200 g). An additional 10 ml of air was injected into the cavity at day −3 to keep the space open. At day 0, Compound I was administered intravenously and one hour later lipopolysaccharide (LPS: 2.5 ml, 2 μg/ml in PBS) was injected into the pouch to produce an inflammatory reaction. Two hours after treatment with LPS, animals were euthanized by $CO_2$ asphyxiation and 5 ml of PBS/heparin (10 U/ml)/indomethacin (36 μg/ml) was injected into the pouch. The pouch fluid was collected and $PGE_2$ was determined in the pouch exudates by ELISA.

Figure 3:
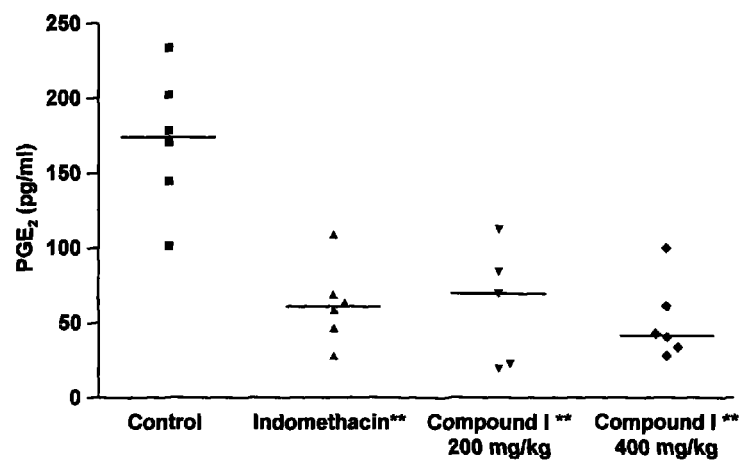
FIG. 3 is a dot graph showing effect of Compound I on PGE2 production in LPS-induced inflammation in rats.

As illustrated in FIG. 3, oral administration of Compound I induces a significant inhibition of $PGE_2$ two hours after administration of LPS. The inhibition achieved by Compound I was similar to that obtained from the positive control indomethacin.

Example 4

Effect of Compound I on Nitric Oxide Production on RAW264.7 Cells

Oxidative stress and inflammation are related to several chronic diseases. Nitric oxide (NO), produced by nitric oxide synthase, has been identified as an important molecule involved in inflammation and sepsis. Inducible nitric oxide synthase (iNOS) is not expressed under normal conditions. However, after exposure to endogenous and exogenous stimulators, it can be induced in various cells such as macrophages, smooth muscle cells and hepatocytes, to trigger several disadvantageous cellular responses, such as inflammation. Hence, the level of iNOS may reflect the degree of inflammation, thereby permitting an evaluation of the effects of drugs on the inflammatory process.

The effect of Compound I on NO production was undertaken in RAW264.7 (macrophage-like) cells. RAW264.7 cells were cultured with 1 μg/ml of LPS and 0.5 ng/ml of interferon in presence or absence of the compound for 16 hours in a humidified atmosphere of 95% air-5% carbon dioxide at 37° C. Nitric oxide measurement in the culture medium was measured using the Griess reagent after an incubation of 30 minutes at room temperature. The absorbance at 548 nm was read and compared with standard solutions of $NaNO_2$. Cell viability was assessed with the addition of 50 μl of MU. After an incubation of 4 hours, the medium was removed and 150 μl of DMSO was added to dissolve the crystals. The optical density of each sample was read at 570 nm against a blank prepared from cell-free wells.

Although not shown, Compound I induced a significant inhibition of NO production (about 50%) in a dose dependent manner.

Example 5

In Vivo Effect of Compound I on Kidney Protection in ⅚ Nephrectomized Rat Model

Demonstration of the in vivo protection effect of Compound I on renal tissue was undertaken in the ⅚ nephrectomized (Nx) rat model using the following procedure. Male 6 week-old Wistar rats were subjected to ⅚ nephrectomy or sham operations. Under fluothane anesthesia, renal ablation was achieved by removing two-thirds of the left kidney followed by a right unilateral nephrectomy 7 days later. Sham rats underwent exposition of the kidneys and removal of the perirenal fat. Twenty-one days after the first operation, rats were randomized in the study by their reduced glomerular filtration rate (GFR) of creatinine indicating a dysfunction of the kidney. Animals that underwent the sham operation were given vehicle (saline) and were used as controls. Nx animals were divided in groups receiving the vehicle or Compound I. Saline or Compound I was given by gastric gavage once daily up to the sacrifice. GFR was measured every three weeks in order to assess the severity of this end-stage renal disease model. Rats were sacrificed at day 190.

Figure 4:
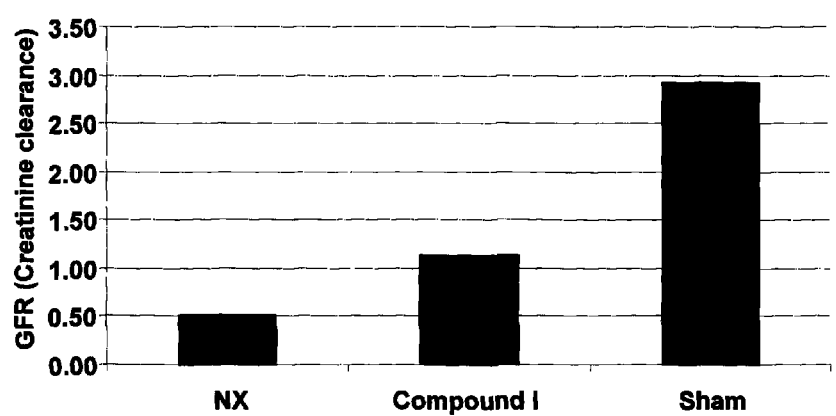
FIG. 4 is a bar graph showing effect of Compound I on GFR (creatine clearance) in ⅚ nephrectomized rats.

FIG. 4 represents the GFR (creatinine clearance) in Nx and Compound I-treated Nx rats compared to sham animals. Compound I improves GFR by two-fold at day 190.

Figure 5:
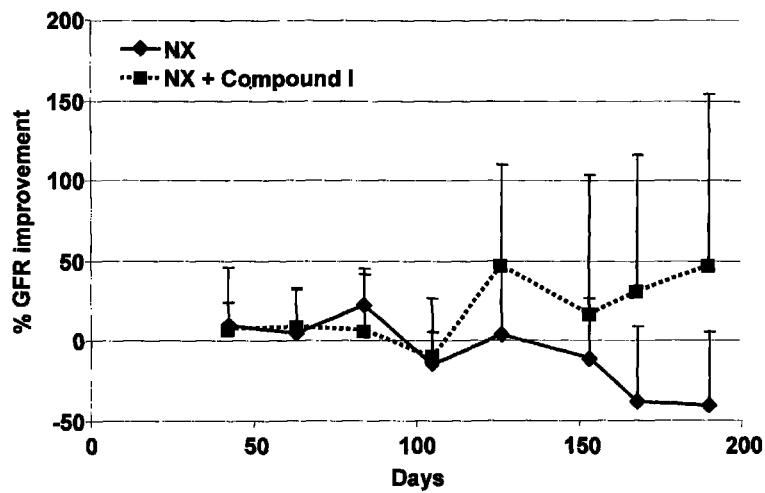
FIG. 5 is a line graph showing effect of Compound I on percentage of GFR improvement in ⅚ nephrectomized rats over a 190-day treatment period.

FIG. 5 represents the improvement of the GFR in Nx and Compound I-treated Nx rats over treatment period compared to the initial GFR (before treatment) at day 21. A 50% improvement of GFR was observed in Compound I-treated Nx rats compared to a 50% deterioration of GFR in Nx rats (control).

Example 6

In Vivo Effect of Compound I on Heart Protection in ⅚ Nephrectomized Rats

Figure 6:
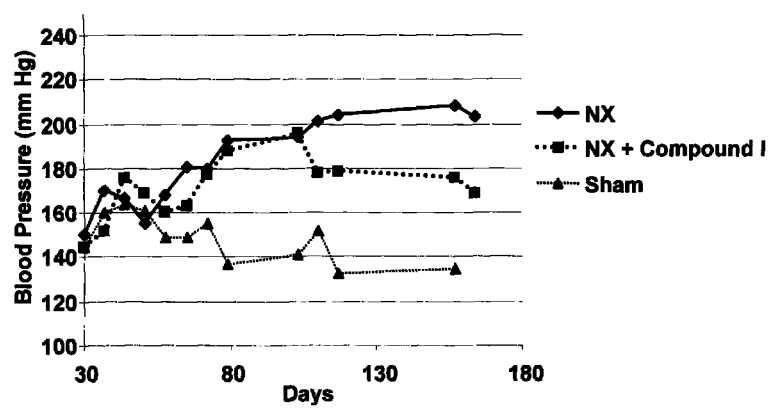
FIG. 6 is a line graph showing cardioprotective effect of Compound I on blood pressure in ⅚ nephrectomized rats.

Demonstration of the in vivo heart protection effect of Compound I was undertaken in the ⅚ nephrectomized (Nx) rat model using the procedure described in example 1. Briefly, heart pressure was recorded with a RTBP 2000™ apparatus (Kent Scientific) in ⅚ nephrectomized rats to demonstrate that Compound I exerts a protective effect on the heart in severely affected 5/6 nephrectomized rats. A significant decrease in blood pressure was observed in Compound I-treated Nx rats (FIG. 6).

Example 7

In Vivo Effect of Compound I on Renal Protection in Doxorubicin-induced Nephrotoxicity Model Demonstration of the in vivo protection effect of oral administration of Compound I was undertaken in the doxorubicin-induced nephrotoxicity model using the following procedure. C57Bl/6 mice (6-10 week-old) were treated with Compound I prophylacticly from day −3 to day 10 or treated therapeutically from day 1 to 10. Nephrotoxicity was induced by an intravenous injection of 10 mg/kg of doxorubicin at day 0. Serum albumin and creatinine were monitored at days 4, 7, 9 and 11.

Figure 7:
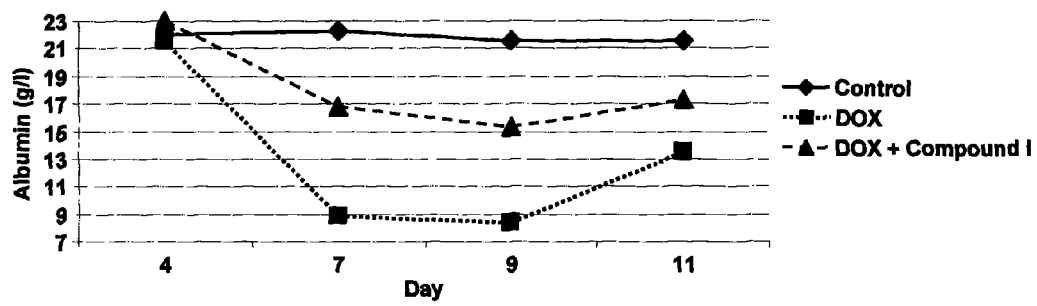
FIG. 7 is a line graph showing nephroprotective effect of Compound I on decreased concentration of serum albumin induced by doxorubicin in mice.

Prophylactic treatment with Compound I inhibits the decrease of serum albumin induced by doxorubicin. Therapeutic treatment with Compound I has no effect on serum albumin level induced by doxorubicin. (FIG. 7).

Figure 8:
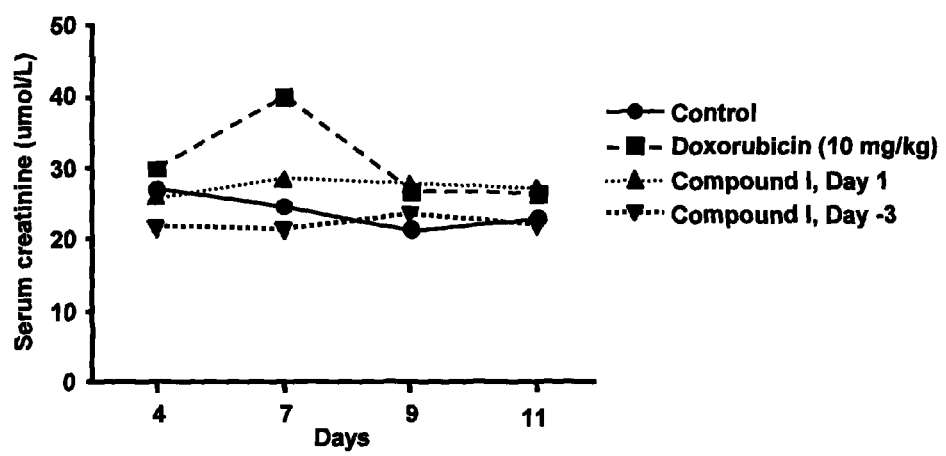
FIG. 8 is a line graph showing nephroprotective effect of Compound I on increased concentration of serum creatinine induced by doxorubicin in mice.

Prophylactic treatment with Compound I inhibits the increase of serum creatinine induced by doxorubicin. Therapeutic treatment with Compound I also inhibits the increase of serum creatinine level induced by doxorubicin. (FIG. 8).

Figure 9:
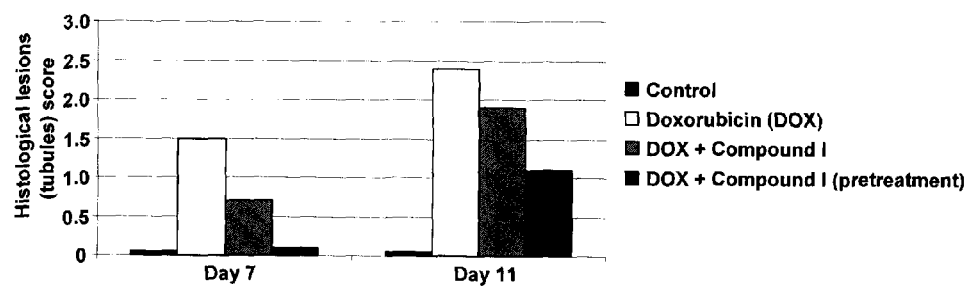
FIG. 9 is a bar graph showing nephroprotective effect of Compound I on histological kidney (tubular) lesions induced by doxorubicin in mice.

Doxorubicin is well known to induce nephro- and cardiotoxicity. FIG. 9 represents the histological kidney lesions score as determined by histochemistry in the doxorubicin-induced nephrotoxicity model. As shown in FIG. 8 doxorubicin induces significant kidney lesions at day 7 and 11. Prophylactic (pre-doxorubicin) and therapeutic (post-doxorubicin) treatments with Compound I reduce the kidney lesions at the tubular level induced by doxorubicin.

Figure 10:
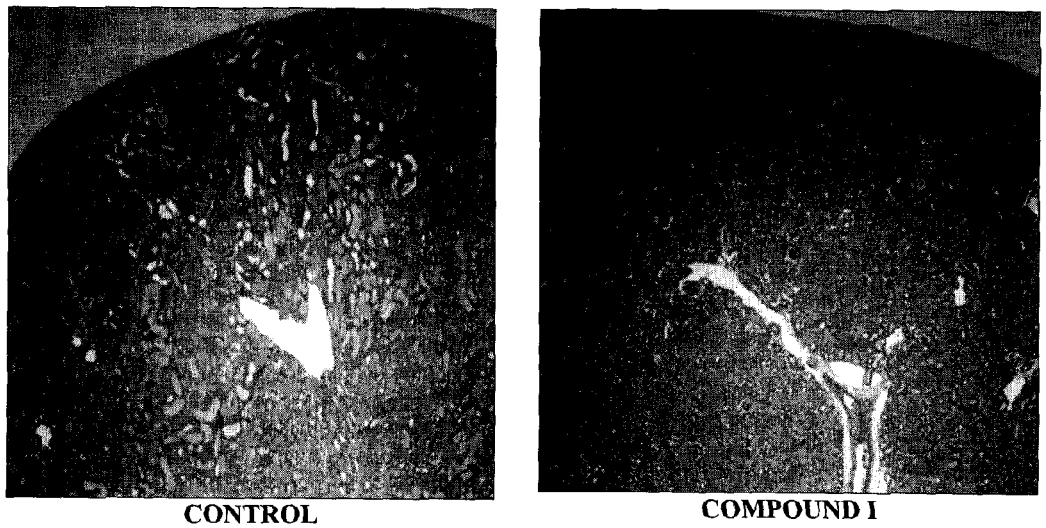
FIG. 10 are pictures showing histological micrographs (40×) of control and Compound I-treated mice in a doxorubicin-induced nephrotoxicity model.

Doxorubicin induces early lesions primarily at the tubular region. Toxicity is further extended to the glomerulus (around day 11 post-doxorubicin). FIG. 10 represents the histological micrographs of doxorubicin-induced lesions in control and Compound I-treated (prophylactic treatment) mice. Doxorubicin induces kidney cell apoptosis, fibrosis, sclerosis and accumulation of proteins in affected tubular regions. Prophylactic or therapeutic treatment with Compound I protects kidney against doxorubicin toxicity.

Figure 11:
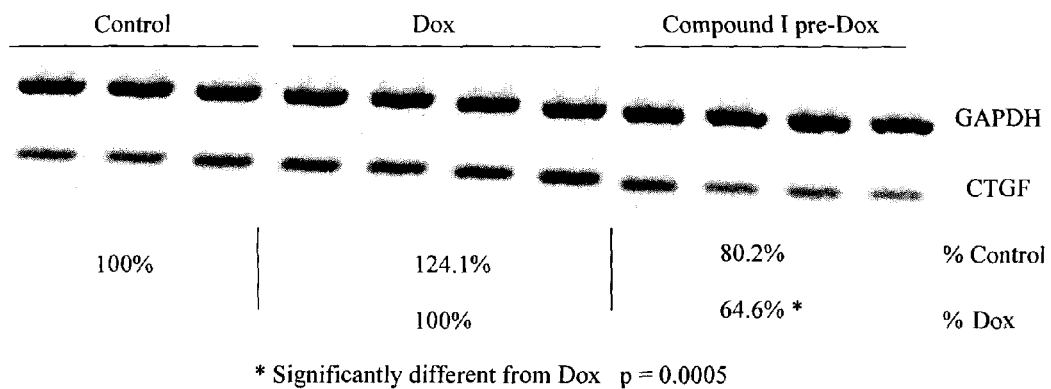
FIG. 11 is a picture of an autoradiogram showing the effect of Compound I on CTGF mRNA expression in kidneys from doxorubicin-treated mice.

The mechanism by which Compound I appears to protect against doxorubicin-induced nephrotoxicity involves inhibition of fibrosis as demonstrated by the significant inhibition of CTGF expression in kidneys treated with Compound I. FIG. 11 illustrates the mRNA expression of CTGF. Doxorubicin increases by 24.1% the mRNA expression of CTGF in kidneys. Pre-treatment with Compound I induces a significant decrease of CTGF expression showing the anti-fibrotic activity of Compound I.

Figure 12:
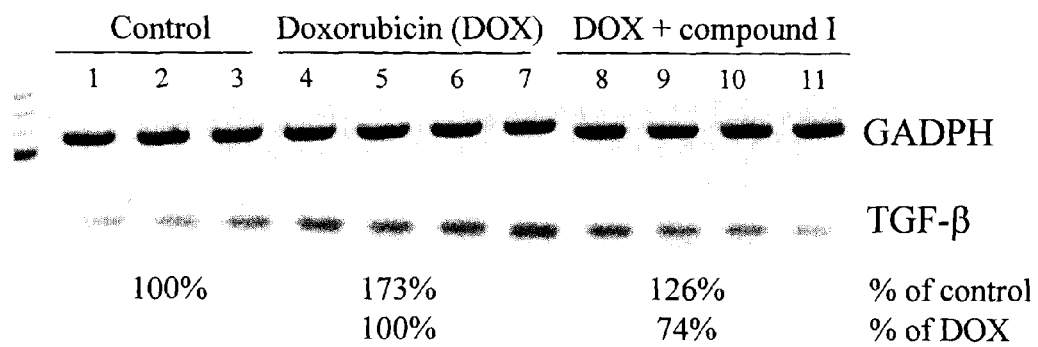
FIG. 12 is a picture of an autoradiogram showing the effect of Compound I on TGF-β mRNA expression in kidneys from doxorubicin-treated mice.

CTGF is also regulated by TGF-β. FIG. 12 illustrates the mRNA expression of TGF-β in kidneys. Doxorubicin increases by 73% the mRNA expression of TGF-β in kidneys. Pre-treatment with Compound I induces a 26% decrease of TGF-β expression.

\*\*\*

Headings are included herein for reference and to aid in locating certain sections. These headings are not intended to limit the scope of the concepts described therein under, and these concepts may be applicable in other sections throughout the entire specification. Thus, the present invention is not intended to be limited to the embodiments shown herein but is to be accorded the widest scope consistent with the principles and novel features disclosed herein.

As used herein and in the appended claims, the singular forms "a", "an", and "the" include plural referents unless the context clearly indicates otherwise. Thus, for example, reference to "a compound" includes one or more of such compounds, and reference to "the method" includes reference to equivalent steps and methods known to those of ordinary skill in the art that could be modified or substituted for the methods described herein.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A salt represented by the formula:

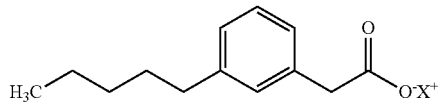

wherein $X^+$ is a base addition salt.

2. The salt, according to claim 1, in which the base addition salt is sodium, potassium, or lithium.

3. The salt, according to claim 1, in which $X^+$ is sodium.

4. A salt represented by the formula:

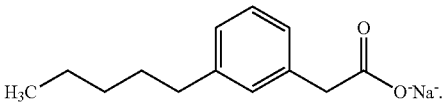

5. A pharmaceutical composition comprising a salt of claim 4, and a pharmaceutically acceptable vehicle.

6. A method of manufacturing a pharmaceutical composition, the method comprising: mixing a salt of claim 4 with a pharmaceutically acceptable vehicle so as to produce the pharmaceutical composition.

7. A method of preventing and/or treating a condition selected from the group consisting of (i) blood disorders (ii) renal disorders and/or renal disorder complications; (iii) inflammatory-related diseases; and (iv) oxidative stress related disorders, said method comprising administering to a human patient in need thereof a pharmacologically effective amount of a salt of claim 4.

8. A process for preparing the sodium salt of 3-pentylphenylacetic acid, the process comprising:
 a) heating a mixture of ethyl [3-bromophenyl]acetate and 1-pentyne in the presence of tetrabutylammonium fluoride hydrate and PdCI$_2$(PPh$_3$)$_2$ to provide ethyl [3-[pentyne-1-yl]phenyl]-acetate;
 b) reducing the ethyl [3-[pentyne-1-yl]phenyl]acetate to provide ethyl [3-[pentyl-1-yl]phenyl]acetate; and
 c) hydrolyzing ethyl [3-[pentyl-1-yl]phenyl]acetate so as to produce the sodium salt of 3-pentylphenylacetic acid.

9. The process, according to claim 8, in which the heating step a) is carried out in a sealed tube.

10. The process, according to claim 9, in which the tube is heated at 80° C. for 2 h.

11. A method for preventing and/or treating a blood disorder in a subject in need thereof, comprising administering to said subject an effective amount of a salt according to claim 1.

12. The method of claim 11, wherein the blood disorder is anemia or neutropenia.

13. The method of claim 11, wherein administration of said composition stimulates hematopoiesis and/or erythropoiesis in the subject.

14. A method for preventing and/or treating a renal disorder and/or a renal disorder complication in a subject in need thereof, comprising administering to said subject an effective amount of a salt according to claim 1.

15. The method of claim 14, wherein the renal disorder is nephropathy.

16. The method of claim 14, wherein the salt is administered for nephroprotection against toxic effects arising from a treatment with a chemotherapeutic agent.

17. The method of claim 16, wherein clearance of creatinine and/or clearance of uric acid is improved in the subject subsequent to said administration.

18. A method for improving kidney function in a human subject in need thereof, comprising administering to said subject an effective amount of a salt according to claim 1.

19. The method according to claim 11, wherein said salt is

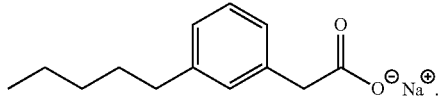

20. A method for preventing and/or treating an inflammatory-related disease in a subject in need thereof, comprising administering to said subject an effective amount of a salt according to claim 1.

21. The method of claim 20, wherein the inflammatory-related disease is an immune mediated inflammatory disease or an autoimmune disease.

22. The method of claim 21, wherein the inflammatory-related disease is selected from the group consisting of arthritis, erythematosus (SLE), idiopathic thrombocytopenic purpura (ITP), glomerulonephritis, vasculitis, psoriatic arthritis, psoriasis, Crohn's disease, inflammatory bowel disease, ankylosing spondylitis, Sjogren's syndrome, Still's disease, uveitis, scleroderma, myositis, Reiter's syndrome, and Wegener's syndrome.

23. A method for nephroprotection against toxic effects arising from a treatment with a chemotherapeutic agent in a subject, comprising administering to said subject an effective amount of a pharmaceutical composition according to claim 5 before and/or following treatment with the chemotherapeutic agent.

24. A method for preventing and/or treating an oxidative stress related disorder in a subject in need thereof, comprising administering to said subject an effective amount of a salt according to claim 1.

25. The method of claim 24, wherein the oxidative stress related disorder is selected from the group consisting of cardiovascular diseases, cancer, diabetes, arthritis, atherosclerosis, Parkinson's disease, heart failure, myocardial infarction, Alzheimer's disease, chronic fatigue syndrome and autoimmune diseases.

\* \* \* \* \*

UNITED STATES PATENT AND TRADEMARK OFFICE
CERTIFICATE OF CORRECTION

PATENT NO. : 8,637,574 B2
APPLICATION NO. : 13/318252
DATED : January 28, 2014
INVENTOR(S) : Boulos Zacharie et al.

Page 1 of 1

It is certified that error appears in the above-identified patent and that said Letters Patent is hereby corrected as shown below:

In the Specification

Column 13,
Line 13, ". OH; arginine" should read --·OH; arginine--.

Column 20,
Line 58, "C57BU6 mice," should read --C57BL/6 mice,--.

Column 22,
Lines 14-15, "50 µl of MU." should read --50 µl of MTT.--.

Signed and Sealed this
Twenty-fourth Day of June, 2014

Michelle K. Lee
*Deputy Director of the United States Patent and Trademark Office*